(12) United States Patent
Cai et al.

(10) Patent No.: US 11,320,417 B2
(45) Date of Patent: May 3, 2022

(54) NANOGAP SENSORS AND METHODS OF FORMING THE SAME

(71) Applicant: GLOBALFOUNDRIES Singapore Pte. Ltd., Singapore (SG)

(72) Inventors: Xinshu Cai, Singapore (SG); Shyue Seng Tan, Singapore (SG); Eng Huat Toh, Singapore (SG); Kiok Boone Elgin Quek, Singapore (SG)

(73) Assignee: GLOBALFOUNDRIES Singapore Pte. Ltd., Singapore (SG)

( * ) Notice: Subject to any disclaimer, the term of this patent is extended or adjusted under 35 U.S.C. 154(b) by 265 days.

(21) Appl. No.: 16/505,733

(22) Filed: Jul. 9, 2019

(65) Prior Publication Data

US 2021/0010997 A1  Jan. 14, 2021

(51) Int. Cl.
*G01N 33/487* (2006.01)
*G01N 27/447* (2006.01)

(52) U.S. Cl.
CPC ... *G01N 33/48721* (2013.01); *G01N 27/4473* (2013.01); *G01N 27/44791* (2013.01)

(58) Field of Classification Search
CPC ......... G01N 33/48721; G01N 27/4473; G01N 27/44791
See application file for complete search history.

(56) References Cited

U.S. PATENT DOCUMENTS

| 8,500,979 B2 | 8/2013 | Elibol et al. |
| 9,322,798 B2 | 4/2016 | Elibol et al. |
| 2016/0184819 A1 | 6/2016 | Naik et al. |
| 2016/0192504 A1* | 6/2016 | Elibol .................. C12Q 1/6869 29/846 |
| 2017/0074819 A1* | 3/2017 | Elibol ................. C23C 18/1633 |

OTHER PUBLICATIONS

Kang et al., "Electrochemical Single-Molecule Detection in Aqueous Solution Using Self-Aligned Nanogap Transducers", ACS Nano, 2013, pp. 10931-10937, vol. 7, No. 12.
Hall et al., "A Nanogap Transducer Array on 32nm CMOS for Electrochemical DNA Sequencing", 2016 IEEE International Solid-State Circuits Conference (ISSCC), 2016, 3 pages, IEEE.

\* cited by examiner

*Primary Examiner* — Luan V Van
*Assistant Examiner* — Caitlyn Mingyun Sun
(74) *Attorney, Agent, or Firm* — Viering Jentschura & Partner MBB (57) ABSTRACT

In a non-limiting embodiment, a device may include a substrate having conducting lines thereon. One or more fin structures may be arranged over the substrate. Each fin structure may include a sensor arranged over the substrate and around the fin structure. The sensor may include a self-aligned first sensing electrode and a self-aligned second sensing electrode arranged around the fin structure. The first sensing electrode and the second sensing electrode each may include a first portion lining a sidewall of the fin structure and a second portion arranged laterally from the first portion. At least the first portion of the first sensing electrode and the first portion of the second sensing electrode may define a sensing cavity of the sensor. The second portion of the first sensing electrode and the second portion of the second sensing electrode may be electrically coupled to the conducting lines.

20 Claims, 8 Drawing Sheets

NANOGAP SENSORS AND METHODS OF FORMING THE SAME

TECHNICAL FIELD

The present disclosure relates generally to electronic sensors and more particularly to nanogap sensors or transducers, and methods of forming the same.

BACKGROUND

Electronic sensors such as nanogap sensors may be used to detect electrochemical tags (e.g., markers or indicators) which has many important applications such as, for example, molecular detection and analysis, molecular diagnostics, disease detection, substance identification, and DNA detection and sequencing. For example, in next generation DNA sequencing, CMOS technology may be employed to form the nanogap sensors. The nanogap sensors are arranged horizontally over an integrated circuit (IC) chip using complementary metal oxide semiconductor (CMOS) processes, where each nanogap sensor includes two planar electrodes arranged over the chip and are separated by a nanoscale gap. Such nanogap sensors employ redox cycling to amplify signals. For example, by properly biasing the two electrodes, redox-active molecules can be repeatedly oxidized at one electrode and reduced at the other, contributing a plurality of electrons to the recorded current and resulting in the net amplification of the signal (e.g., presence of the redox-active molecules). However, existing nanogap sensors have finite dead volumes which interrupts the redox process. For example, a dead volume may be formed by non-overlap regions of the two electrodes. The dead volume causes the redox process to stop when molecules are located at the dead volumes, which reduces and limits the redox cycling efficiency of the nanogap sensors such as in electrochemical DNA sequencing and lowers the observed signal (e.g., current). Furthermore, existing processes for forming the nanogap sensors are complicated and require additional masks and polishing steps.

From the foregoing discussion, it is desirable to provide an electronic sensor which addresses the above-mentioned challenges.

SUMMARY

Embodiments generally relate to semiconductor devices and method for forming the semiconductor devices. According to various non-limiting embodiments, a device may include a substrate having conducting lines thereon. One or more fin structures may be arranged over the substrate. Each fin structure may include a sensor arranged over the substrate and around the fin structure. The sensor may include a self-aligned first sensing electrode and a self-aligned second sensing electrode arranged around the fin structure. The first sensing electrode and the second sensing electrode each may include a first portion lining a sidewall of the fin structure and a second portion arranged laterally from the first portion. At least the first portion of the first sensing electrode and the first portion of the second sensing electrode may define a sensing cavity of the sensor. The second portion of the first sensing electrode and the second portion of the second sensing electrode may be electrically coupled to the conducting lines.

According to various non-limiting embodiments, a device may include a substrate having conducting lines thereon. One or more fin structures may be arranged over the substrate. Each of the one or more fin structures may include a sensor arranged around the fin structure over the substrate. The sensor may include a self-aligned first sensing electrode and a self-aligned second sensing electrode arranged around the fin structure. The first sensing electrode and the second sensing electrode may define a vertical sensing cavity of the sensor around the fin structure, and the first sensing electrode and the second sensing electrode may be electrically coupled to the conducting lines.

According to various embodiments, a method of forming a device is provided. The method may include providing a substrate having conducting lines thereon. The method may include arranging one or more fin structures over the substrate, and arranging a sensor over the substrate and around each fin structure of the one or more fin structures. Arranging the sensor may include forming a self-aligned first sensing electrode and a second sensing electrode around the one or more fin structures. The first sensing electrode and the second sensing electrode each includes a first portion lining a sidewall of the fin structure and a second portion arranged laterally from the first portion. At least the first portion of the first sensing electrode and the first portion of the second sensing electrode define a sensing cavity of the sensor, and the second portion of the first sensing electrode and the second portion of the second sensing electrode are electrically coupled to the conducting lines.

These and other advantages and features of the embodiments herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following.

DETAILED DESCRIPTION

The following detailed description refers to the accompanying drawings that show, by way of illustration, specific details and embodiments in which the embodiments may be practiced. These embodiments are described in sufficient detail to enable those skilled in the art to practice the embodiments. Other embodiments may be utilized and structural, logical, and electrical changes may be made without departing from the scope of the invention. The various embodiments are not necessarily mutually exclusive, as some embodiments can be combined with one or more other embodiments to form new embodiments.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Approximating language, as used herein throughout the specification and claims, may be applied to modify any quantitative representation that could permissibly vary without resulting in a change in the basic function to which it is related. Accordingly, a value modified by a term or terms, such as "about," is not limited to the precise value specified. In some instances, the approximating language may correspond to the precision of an instrument for measuring the value.

The terminology used herein is for the purpose of describing particular examples only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include (and any form of include, such as "includes" and "including"), and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more steps or elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

As used herein, the term "connected," when used to refer to two physical elements, means a direct connection between the two physical elements. The term "coupled," however, can mean a direct connection or a connection through one or more intermediary elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable or suitable. For example, in some circumstances, an event or capacity can be expected, while in other circumstances the event or capacity cannot occur—this distinction is captured by the terms "may" and "may be."

Embodiments of the present disclosure generally relate to electronic sensors that are capable of detecting biological reactions and/or molecules and that exhibit high sensitivity. According to various non-limiting embodiments, the sensors enable high-density electrochemical detection, such as for electrochemical DNA sequencing. The sensors may be arranged over a substrate having conducting lines. The conducting lines couple the sensors to electric circuits. The substrate may be an integrated circuit (IC) chip in a non-limiting embodiment. According to various non-limiting embodiments, one or more fin structures may be arranged over the substrate. Each fin structure may include a sensor arranged around the fin structure. The sensor may include a self-aligned first sensing electrode and a self-aligned second sensing electrode arranged around the fin structure. The first sensing electrode and the second sensing electrode may each include a first portion lining a sidewall of the fin structure and a second portion arranged laterally from the first portion. According to various non-limiting embodiments, at least the first portion of the first sensing electrode and the first portion of the second sensing electrode may define a sensing cavity (or channel) of the sensor, and the second portion of the first sensing electrode and the second portion of the second sensing electrode may be electrically coupled to the conducting lines.

According to various non-limiting embodiments, the electronic sensors may be nanogap transducers. For example, the first sensing electrode and the second sensing electrode may be separated by a gap in the nanoscale range to form a nanogap channel.

According to various non-limiting embodiments, each of the electronic sensors may have a vertical nanogap structure. For example, the sensing cavity may be arranged vertically with respect to a top surface of the substrate. Said differently, the first sensing electrode and the second sensing electrode define a vertical sensing cavity of the sensor around the fin structure, and the first sensing electrode and the second sensing electrode are electrically coupled to the conducting lines. According to various non-limiting embodiments, each of the electronic sensors may further include a lateral portion extending from the vertical sensing cavity. The vertical sensing cavity and/or the lateral portion of the sensing cavity may have or exhibit a zero dead volume. Such sensors advantageously enable higher redox efficiency as well as higher sensitivity for various applications. For example, the first sensing electrode and the second sensing electrode may be used detect electrochemical tags by redox cycling. The sensors as will be described may be formed by a more simple process relative to conventional manufacturing steps, as well as less processing steps which reduces manufacturing costs. For example, the sensors may be fabricated with lower mask count and/or planarization (e.g., chemical mechanical polishing) steps.

According to various non-limiting embodiments, each of the electronic sensors may include a self-aligned double sensing plate around the fin structure, forming double sensing cavities (or channels) as will be described. Accordingly, a high density sensor array may be provided where each sensor includes double sensing channels.

The sensors may be incorporated into or used with various applications such as, for example, molecular detection and analysis, molecular diagnostics, disease detection, substance identification, and DNA detection and sequencing, security, or relate to other types of devices. In a non-limiting example, the sensors in the present disclosure may be described with respect to sensing or detecting molecules by redox cycling such as in DNA sequencing; however, it should be understood that the sensors may be employed in various other applications.

Figure 1A:
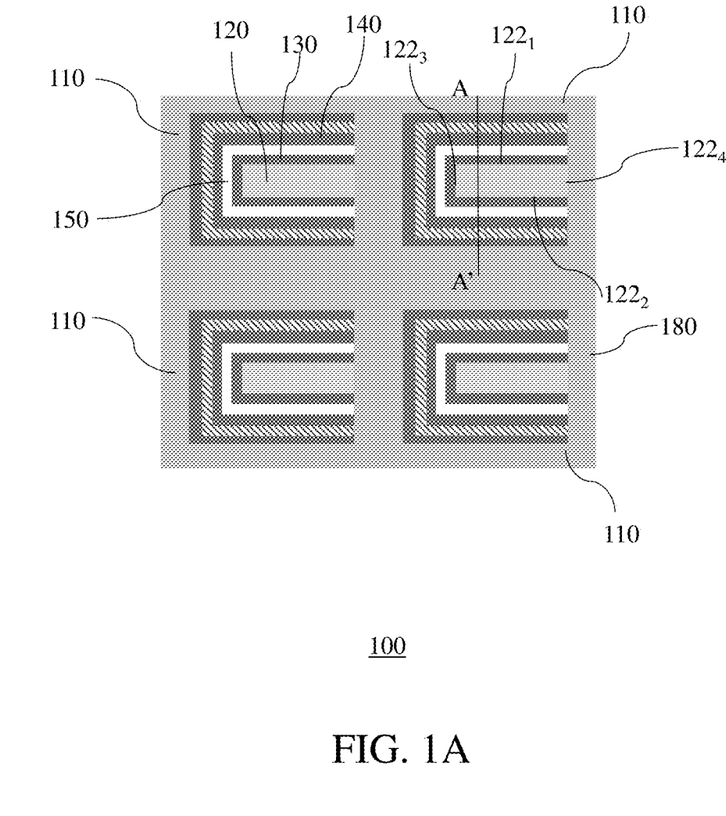
FIGS. 1A-1B show exemplary top views of embodiments of a device.
Figure 1B:
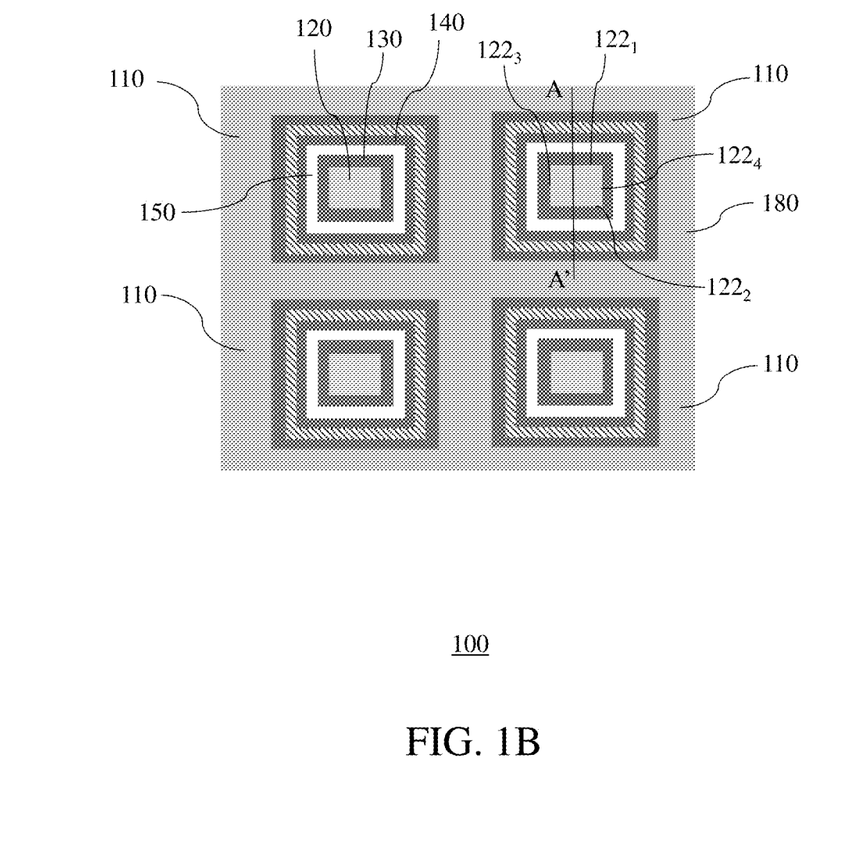

FIGS. 1A-1B show exemplary top views of non-limiting embodiments of a device 100. The device 100 may include one or more sensors 110. As illustrated in FIGS. 1A and 1B, the device 100 may include an array of sensors 110. For example, the sensors may be arranged in rows and columns of an array. Illustratively, two rows and two columns of sensors are shown. It is understood that the array of sensors 110 may include other number of sensors and may be arranged in various other configurations.

The sensor(s) may be arranged over a substrate (not shown in FIG. 1). The substrate, for example, may be a semiconductor substrate, such as a silicon substrate. According to various non-limiting embodiments, the substrate may be an IC chip having electric circuits. For example, the substrate may be a CMOS substrate having electric circuits. The electric circuits may be formed by CMOS processing, in a non-limiting embodiment. Providing a bare substrate may also be useful. The substrate may be arranged with conducting lines. The conducting lines may electrically connect the sensor(s) 110 to electric circuits such as in the substrate to perform the desired functions. The conducting lines, for example, may be top metal lines from CMOS processing.

According to various non-limiting embodiments, one or more fin structures 120 may be arranged over the substrate. In some embodiments, the one or more fin structures may be an array of fin structures arranged over the substrate. The fin structure(s) 120 may each include a sensor 110 arranged around the fin structure. According to various non-limiting embodiments, the sensor(s) 110 may have an open configuration, as illustrated in FIG. 1A. For example, a sensor 110 does not completely surround a fin structure 120 in the open configuration. For example, a sensing cavity or electrodes of the sensor 110 does not completely surround the fin structure 120 in the open configuration. In other embodiments, the sensor(s) 110 may have a closed configuration, as illustrated in FIG. 1B. For example, a sensor 110 completely surrounds a fin structure 120 in the closed configuration. In other words, the sensor 110 continuously surrounds the fin structure 120 in the closed configuration. For example, a sensing cavity or electrodes of the sensor 110 completely surrounds the fin structure 120 in the closed configuration. The open or closed configuration may be used depending on application, such as direction of insertion of fluid into a sensing cavity of the sensor, in a non-limiting example.

Figure 2A:
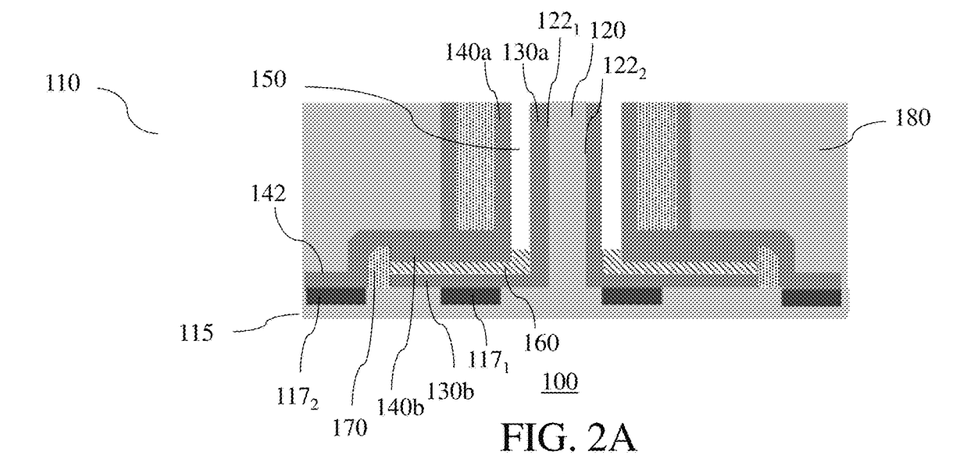
FIGS. 2A-2B show cross-sectional views of embodiments of the device.
Figure 2B:
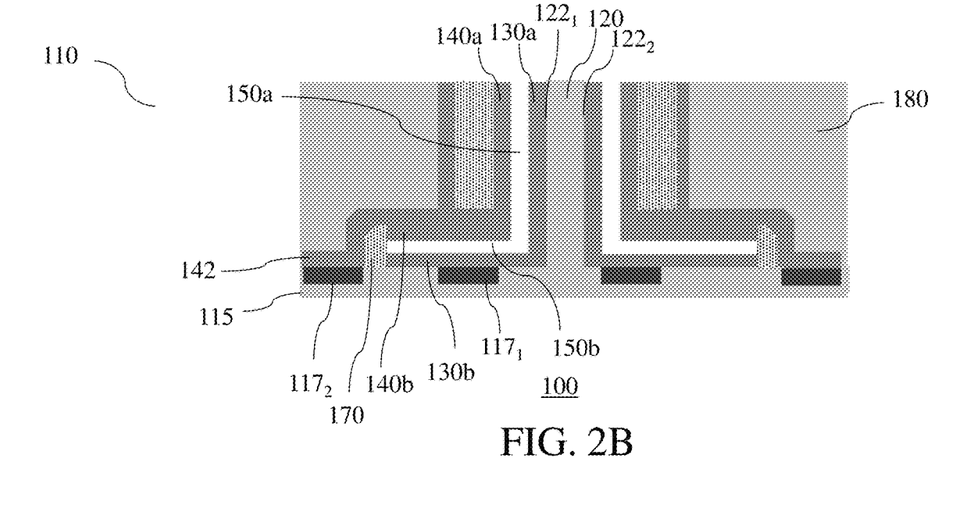

FIGS. 2A-2B show cross-sectional views of embodiments of the device 100 along the line AA'. The cross-sectional views illustrate a sensor 110 arranged around a fin structure 120. For example, the fin structure 120 may be a fin extending from a substrate 115 as described. The fin structure 120 may have a pillar configuration extending from a surface of the substrate. The fin structure 120 may have a rectangular cross-section in a non-limiting example. According to various non-limiting embodiments, the fin structure may have the configuration of a three-dimensional (3D) rectangular prism. Other configurations such as a cylinder may also be used. The fin structure 120 may be formed of a dielectric material such as silicon oxide (e.g., $SiO_2$), low-k dielectric (e.g., with addition of fluorine to oxide (SiOF), carbon-doped oxide (CDO, SiOC, or SiCOH) in a non-limiting example. Providing other types and configuration of the fin structure 120 may also be useful.

As illustrated in FIGS. 2A and 2B, the substrate 115 may include conducting lines 117 for electrically coupling the sensor 110 to electric circuits in the substrate. The conducting lines 117 may be formed of electrically conductive material such as copper, copper alloy, aluminum, tungsten or a combination thereof, in a non-limiting example. The conducting lines 117 may be isolated and surrounded by one or more dielectric materials which are arranged over the substrate 115, such as low-k dielectric (e.g., SiCOH), silicon oxide, silicon nitride and etc.

According to various non-limiting embodiments, the sensor 110 includes a self-aligned first sensing electrode 130 and a self-aligned second sensing electrode 140 arranged around the fin structure 120. The first sensing electrode 130 and the second sensing electrode 140 may be formed conformally around the sidewall(s) of the fin structure 120. For example, the first sensing electrode 130 and the second sensing electrode 140 'self-aligns' around the fin structure 120 without the use of an additional mask. For example, the first sensing electrode 130 and the second sensing electrode 140 'self-aligns' around the fin structure 120 using a single mask. In other words, the self-aligned first sensing electrode 130 and the self-aligned second sensing electrode 140 may be formed (e.g., deposited and patterned) over the substrate using a single mask in the same lithography and etch process. The first sensing electrode 130 and the second sensing electrode 140 may be an electrode pair of a sensor 110. The first sensing electrode 130 and the second sensing electrode 140 may define a sensing cavity 150 of the sensor 110, i.e. the sensing cavity 150 is arranged between the first sensing electrode 130 and the second sensing electrode 140. The sensing cavity 150 may be arranged conformally around the fin structure 120. Said differently, the sensing cavity 150 may be self-aligned around the fin structure 120 without the use of an additional mask. The sensing cavity may be a channel in a non-limiting embodiment. The first sensing electrode 130 and the second sensing electrode 140 may be separated by a gap having a distance ranging from about 1 nm to about 100 nm, where the gap forms a nanogap channel of the sensor, which is the sensing cavity 150.

According to various non-limiting embodiments, the first sensing electrode 130 and the second sensing electrode 140 may be configured to detect electrochemical tags passing therebetween and flowing in the nanogap channel, for example, by an electrical signal (e.g., current) where the electrochemical tags generate on the first sensing electrode 130 and the second sensing electrode 140. For example, a molecule or chemical species may undergo an electrochemical or chemical reaction, such as redox cycling, by applying an electric potential to the first sensing electrode 130 and the second sensing electrode 140.

According to various non-limiting embodiments, the first sensing electrode 130 and the second sensing electrode 140 may each include a first portion (i.e., 130a and 140a) lining a sidewall of the fin structure 120 and a second portion (i.e., 130b and 140b) arranged laterally from the first portion. According to various non-limiting embodiments, at least the first portion 130a of the first sensing electrode and the first portion 140a of the second sensing electrode define the sensing cavity 150 of the sensor 110. As illustrated in FIG. 2A, the first portion 130a of the first sensing electrode and the first portion 140a of the second sensing electrode define the sensing cavity 150 of the sensor 110, while the second portion 130b of the first sensing electrode and the second portion 140b of the second sensing electrode are separated by a sacrificial material 160. The sacrificial material 160 fills a gap between the second portion 130b of the first sensing electrode and the second portion 140b of the second sensing electrode. The sensing cavity 150 defined between the first portion 130a of the first sensing electrode and the first portion 140a of the second sensing electrode may be a vertical sensing cavity of the sensor 110. The sacrificial material 160 may be a dielectric material such as silicon nitride (e.g., $Si_3N_4$), in a non-limiting example.

According to another non-limiting embodiment, the sacrificial material 160 may be removed from the gap between the second portion 130b of the first sensing electrode and the second portion 140b of the second sensing electrode to utilize the second portion 130b and the second portion 140b as a sensing cavity. As illustrated in FIG. 2B, the first portion 130a and the second portion 130b of the first sensing electrode and the first portion 140a and the second portion 140b of the second sensing electrode define the sensing cavity 150 of the sensor 110. For example, the first portion 130a of the first sensing electrode and the first portion 140a of the second sensing electrode defines a vertical sensing cavity (or nanogap channel) 150a of the sensor 110, while the second portion 130b of the first sensing electrode and the second portion 140b of the second sensing electrode further defines a lateral portion 150b of the sensing cavity (or nanogap channel). In other words, the lateral portion of the first sensing electrode and the second sensing electrode may be further utilized to form a lateral portion 150b of the sensing cavity. Providing the second portion or lateral portion of the sensing cavity in addition to the first portion or vertical sensing cavity enables the sensor 110 to contain more volume of fluid and therefore molecules (or redox active species) for detection, in a non-limiting example.

In a non-limiting embodiment, the first portion 130a of the first sensing electrode and the first portion 140a of the second sensing electrode define the sensing cavity 150 with a zero dead volume. In other words, the sensing cavity 150 as defined has no regions of non-overlap between the first sensing electrode and the second sensing electrode (e.g., the first portion 130a of the first sensing electrode and the first portion 140a of the second sensing electrode). This advantageously enhances, for example, redox cycling efficiency of the sensor(s) 110 compared to conventional nanogap transducers used in electrochemical DNA sequencing, and facilitates a higher or stronger observed signal (e.g., current). In another non-limiting embodiment, the first portion 130a and the second portion 130b of the first sensing electrode and the first portion 140a and the second portion 140b of the second sensing electrode define the sensing cavity 150 (e.g., vertical sensing cavity 150a and lateral portion 150b of the sensing cavity) with a zero dead volume.

Further, as illustrated in FIGS. 2A and 2B, the first sensing electrode 130 and the second sensing electrode 140 may define a first sensing cavity over a first sidewall $122_1$ of the fin structure 120 and a second sensing cavity over a second sidewall $122_2$ of the fin structure 120. For example, referring back to FIGS. 1A and 1B, each fin structure 120 may include a first sidewall $122_1$ and a second sidewall $122_2$. The first sidewall $122_1$ and the second sidewall $122_2$ may be opposing sidewalls. It may be appreciated that each fin structure 120 may further include other numbers of sidewalls such as a third sidewall $122_3$ and a fourth sidewall $122_4$. For example, the pair of first sensing electrode 130 and the second sensing electrode 140 forms double sensing cavities 150 (or nanogap channels) around each fin structure 120. Accordingly, the device 100 may be provided with a high density sensor(s) having double sensing channels. Such sensing cavity 150 as defined by the first sensing electrode 130 and the second sensing electrode 140 around the fin structure 120 further enables a stronger observed signal (e.g., at least twice the redox current may be obtained as compared to conventional nanogap transducers having two horizontal electrodes over a CMOS chip).

The first sensing electrode 130 and the second sensing electrode 140 may be electrically coupled to the conducting lines $117_1$ and $117_2$. According to various non-limiting embodiments, the first sensing electrode is electrically coupled to a first conducting line(s) $117_1$, and the second sensing electrode is electrically coupled to a second conducting line(s) $117_2$. The first sensing electrode 130 and the second sensing electrode 140 may be independently biased. In addition, a plurality of sensors 110 over the substrate 115 may be independently biased.

As illustrated in FIGS. 2A and 2B, the second portion 130b of the first sensing electrode and the second portion 140b of the second sensing electrode may be electrically coupled to the conducting lines 117. According to various non-limiting embodiments, the second portion 130b of the first sensing electrode may directly overlap and contact the first conducting line(s) $117_1$, while the second sensing electrode may include an extension region 142 to contact the second conducting line(s) $117_2$. The extension region 142 of the second sensing electrode may be spaced apart from the first sensing electrode by a dielectric spacer 170. As illustrated in FIGS. 2A and 2B, the dielectric spacer 170 separates the extension region 142 of the second sensing electrode from an end of the second portion 130b of the first sensing electrode, which prevents short circuit between the first sensing electrode 130 and the second sensing electrode 140. The dielectric spacer 170 may be formed of a dielectric material such as an oxide material, such as, including but not limited to silicon oxide ($SiO_2$), in a non-limiting example.

The first sensing electrode 130 and the second sensing electrode 140 may be formed of electrically conductive materials including, but not limited to, platinum, gold, silver, alloys thereof, or combinations thereof. The first sensing electrode 130 and the second sensing electrode 140 may be formed of different materials or the same material.

A passivation layer 180 may surround and isolate the sensor(s) 110. The passivation layer 180 may be formed of one or more dielectric materials such as silicon oxide, silicon nitride, or combinations thereof. The passivation layer 180 and the fin structure 120 may have a substantially planar top surface in a non-limiting embodiment.

FIGS. 3A-3H show simplified cross-sectional views of an embodiment of a process 300 for forming a device. According to various non-limiting embodiments, the process forms one or more sensors over the same substrate. The device formed, for example, is similar or the same as that shown and described in FIGS. 1A-1B and FIG. 2A. As such, common elements may not be described or described in detail.

Figure 3A:
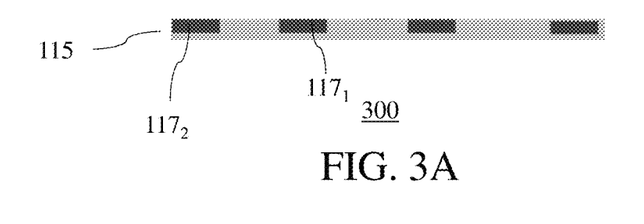
FIGS. 3A-3H show simplified cross-sectional views of an embodiment of a process for forming a device.

For simplicity of discussion and in interest of brevity, the processing of a substrate 115 to form electric circuits and conducting lines are not shown. Referring to FIG. 3A, a substrate 115 having conducting lines 117 thereon is provided. The conducting lines 117 may be formed by CMOS processing, in a non-limiting embodiment. The conducting lines 117 may be coupled to electric circuits.

Figure 3B:
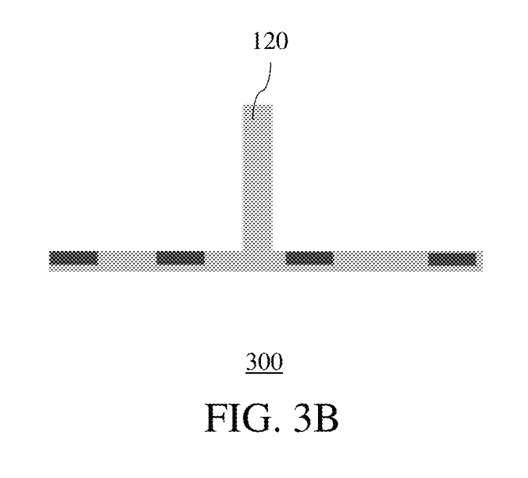

One or more fin structures 120 may be arranged over the substrate. As shown in FIG. 3B, a fin structure 120 is arranged over the substrate 115. However, it should be understood that an array of fin structures may be arranged over the substrate. The fin structure(s) 120 may be formed by depositing a dielectric layer over the substrate and patterning the dielectric layer using, for example, mask and etch to form the fin structure(s) 120. For example, a single mask may be used to form the fin structure(s) 120.

A sensor may be arranged over the substrate 115 and around each fin structure 120. Arranging the sensor includes forming a self-aligned first sensing electrode and a self-aligned second sensing electrode around the fin structure(s) 120.

Figure 3C:
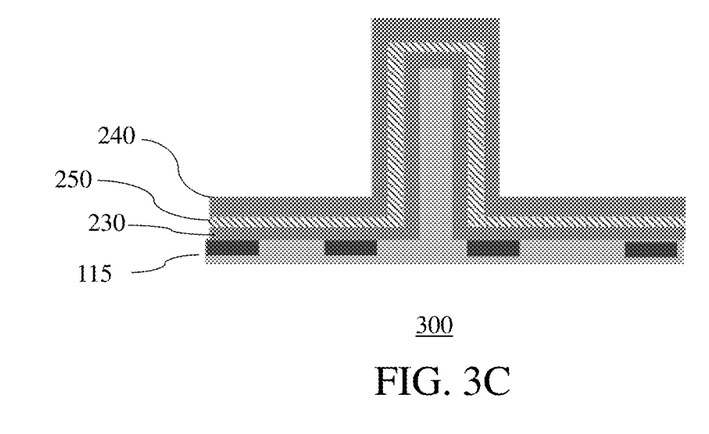

As illustrated in FIG. 3C, a first electrode layer 230 may be deposited over the fin structure(s) 120. The first electrode layer 230 may be formed by physical vapor deposition (PVD), in a non-limiting example. A sacrificial layer 250 may be deposited over the first electrode layer 230. The sacrificial layer 250 may be formed by atomic layer deposition (ALD), in a non-limiting example. A second electrode layer 240 may be deposited over the sacrificial layer 250. The second electrode layer 240 may be formed by PVD, in a non-limiting example. Other deposition techniques may also be useful as known to those skilled in the art. At least a portion of the sacrificial layer 250 may be subsequently removed to form the sensing cavity of a sensor.

Figure 3D:
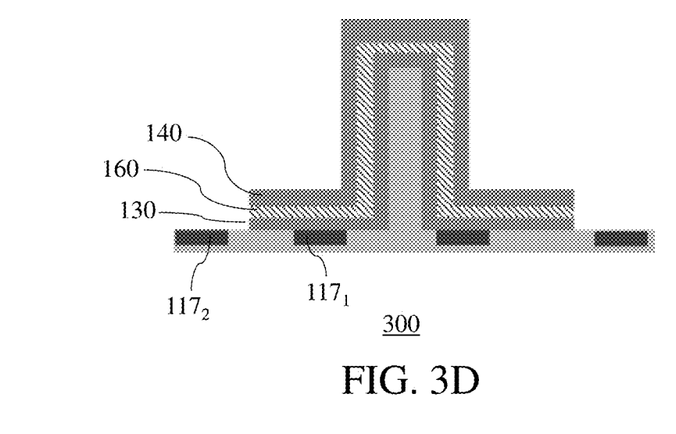

At least a portion of first electrode layer 230, the sacrificial layer 250 and the second electrode layer 240 may be removed from the substrate to define the first sensing electrode and the second sensing electrode, as shown in FIG. 3D. According to various non-limiting embodiments, the first electrode layer 230, the sacrificial layer 250, and the second electrode layer 240 may be patterned by mask and etch technique to define the first sensing electrode and the second sensing electrode. According to various non-limiting embodiments, a single mask may be used to define the first sensing electrode 130 and the second sensing electrode 140. The first sensing electrode 130 and the second sensing electrode 140 are aligned one to another without using an additional mask. The first sensing electrode 130 and the second sensing electrode 140 are self-aligned to one another and around the fin structure 120. The sacrificial layer 160 is sandwiched between the defined first sensing electrode 130 and the second sensing electrode 140, and aligned to the sensing electrodes 130 and 140. The self-aligned first sensing electrode 130 and the self-aligned second sensing electrode 140 may be used to form a sensing cavity with a zero dead volume (e.g., no regions of non-overlap between the first sensing electrode and the second sensing electrode).

The first sensing electrode may be electrically coupled to a first conducting line $117_1$ and the second sensing electrode may be electrically coupled to a second conducting line $117_2$. As illustrated in FIG. 3D, the first sensing electrode is in contact with the first conducting line $117_1$. The second sensing electrode may be electrically coupled to the second conducting line $117_2$ by forming a dielectric spacer around the defined first sensing electrode and second sensing electrode, and forming an extension region of the second sensing electrode over the dielectric spacer to contact the second conducting line $117_2$.

Figure 3E:
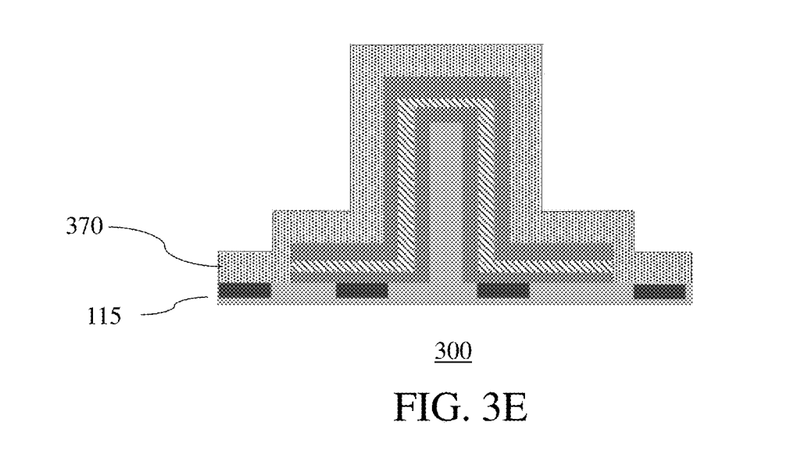
Figure 3F:
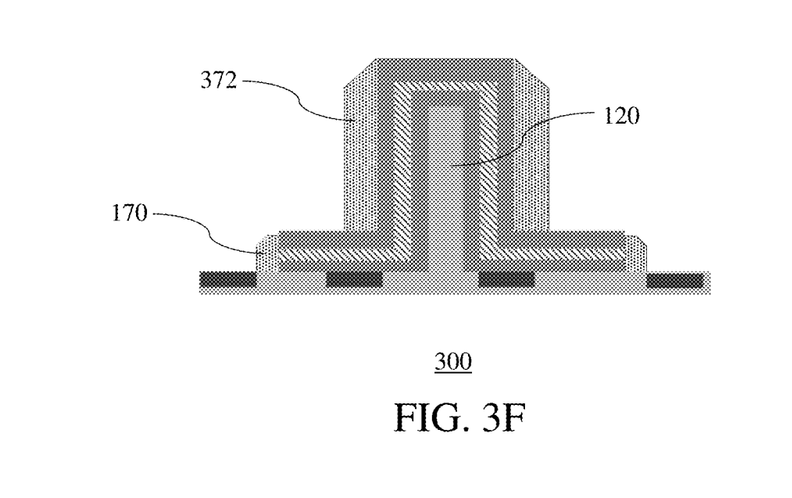

The dielectric spacer may be formed adjacent to the ends of the second portions (or lateral portions) of the first sensing electrode and the second sensing electrode. As illustrated in FIG. 3E, a spacer dielectric layer 370 may be deposited over the substrate 115. The spacer dielectric layer 370 may be formed by chemical vapor deposition (CVD), in a non-limiting example. An etch such as a reactive ion etch (RIE) may be performed to form the dielectric spacer 170, as shown in FIG. 3F. For example, the dielectric spacer 170 may be arranged over the substrate without using a mask. Other types of etching techniques may also be useful. The dielectric spacer 170 isolates the first sensing electrode and the second sensing electrode (e.g., in the lateral or horizontal portions of the first sensing electrode and the second sensing electrode). In a non-limiting embodiment, some material of the spacer dielectric layer 370 may remain over the sidewall(s) of the fin structure 120 (or line first portions or vertical portions of the second sensing electrode) after the etch, forming a dielectric spacer 372 of the second sensing electrode.

Figure 3G:
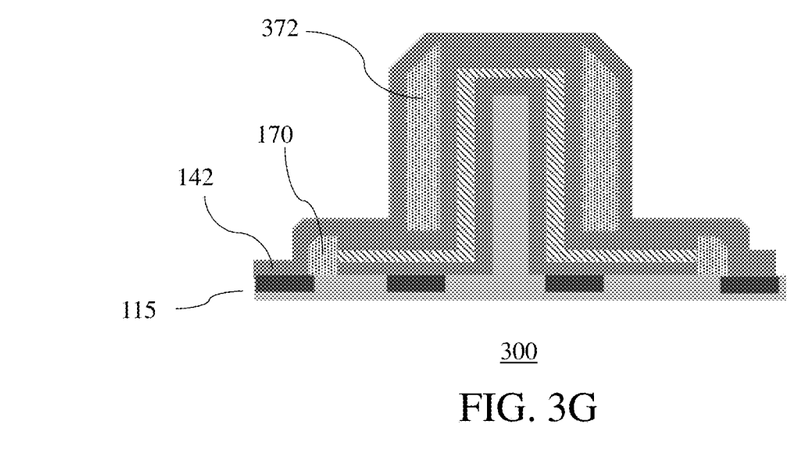

A third electrode layer may be deposited over the substrate 115, forming the extension region 142 of the second sensing electrode as shown in FIG. 3G. The third electrode layer may be the same or different material from the second electrode layer 240 as described with respect to FIG. 3C. As shown in FIG. 3G, the extension region 142 of the second sensing electrode contacts the second conducting line $117_2$ and is electrically connected thereto.

A passivation layer 180 may be formed over the substrate 115 and the sensing electrodes. For example, the passivation layer 180 isolates one or more sensors formed over the substrate. The passivation layer 180 may be formed, for example, by CVD. A planarization process, such as chemical mechanical polishing (CMP) in a non-limiting example, may be performed. In a non-limiting embodiment, the planarization process provides a substantially planar top surface between the fin structure 120 and the passivation layer 180.

Figure 3H:
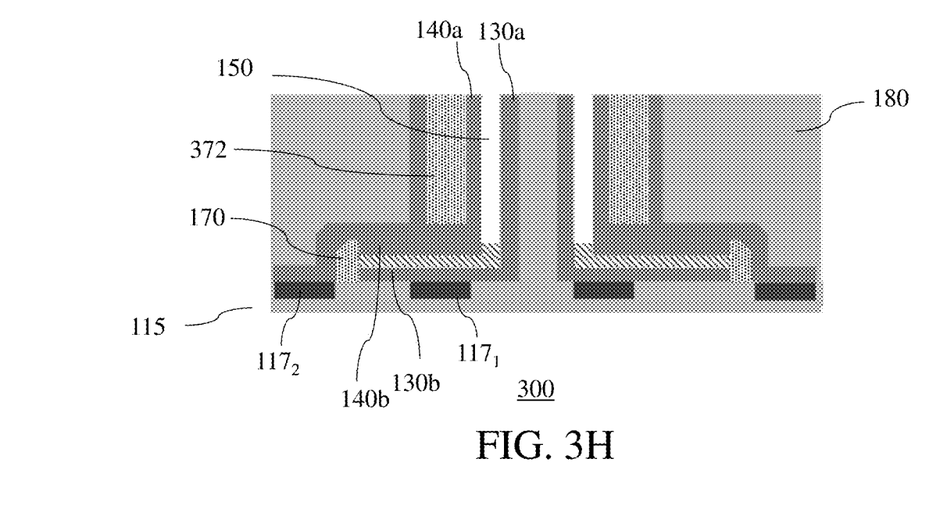

At least a portion of the sacrificial layer between the first sensing electrode 130 and the second sensing electrode 140 may be removed to form a sensing cavity. The sensing cavity may be formed around the fin structure 120. According to various non-limiting embodiments, the sacrificial layer between the first portion 130a of the first sensing electrode and the first portion 140a of the second sensing electrode is removed, while leaving the sacrificial layer between the second portion 130b of the first sensing electrode and the second portion 140b of the second sensing electrode. The sacrificial layer may be removed by an etch, such as a wet etch (e.g., using phosphoric acid, $H_3PO_4$), in a non-limiting example. The etch to remove the sacrificial layer may be controlled by timing depending on the depth or amount of the sacrificial layer to be removed, in a non-limiting embodiment. As illustrated in FIG. 3H, the first sensing electrode and the second sensing electrode each includes a first portion (e.g., 130a and 140a) lining a sidewall of the fin structure 120 and a second portion (e.g., 130b and 140b) arranged laterally from the first portion. At least the first portion 130a of the first sensing electrode and the first portion 140a of the second sensing electrode define a sensing cavity 150 of the sensor, and the second portion 130b of the first sensing electrode and the second portion 140b of the second sensing electrode are electrically coupled to the conducting lines $117_1$ and $117_2$. The first portion 130a of the first sensing electrode and the first portion 140a of the second sensing electrode define the sensing cavity 150 with a zero dead volume. For example, a self-aligned sensing cavity 150 of the sensor(s) 110 may be formed.

Figure 4A:
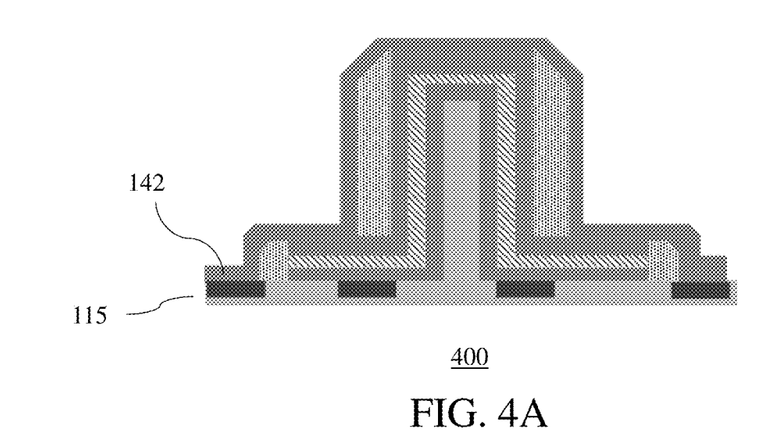
FIGS. 4A-4B show simplified cross-sectional views of another embodiment of a process for forming a device.
Figure 4B:
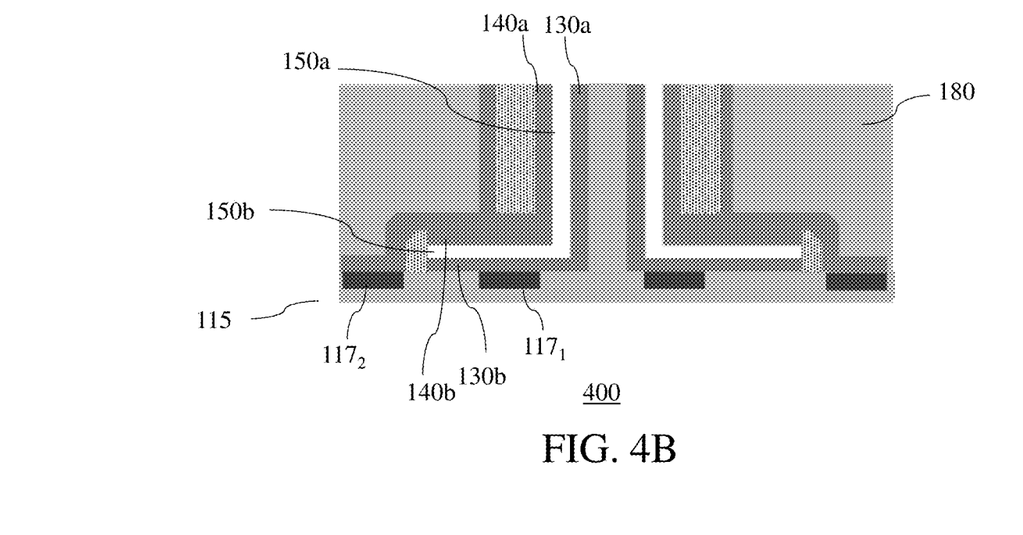

FIGS. 4A-4B show simplified cross-sectional views of another embodiment of a process 400 for forming a device. According to various non-limiting embodiments, the process forms one or more sensors over the same substrate. The device formed, for example, is similar or the same as that shown and described in FIGS. 1A-1B and FIG. 2B. As such, common elements may not be described or described in detail.

The process 400 may be similar to process 300 as described above. For example, FIG. 4A illustrates the substrate 115 which is at the stage of processing as described in FIG. 3G. A passivation layer 180 may be formed over the substrate 115 and the sensing electrodes. A planarization process, such as CMP in a non-limiting example, may be performed. In a non-limiting embodiment, the planarization process provides a substantially planar top surface between the fin structure 120 and the passivation layer 180.

According to various non-limiting embodiments, the sacrificial layer between the first portion 130a and the second portion 130b of the first sensing electrode and the first portion 140a and the second portion 140b of the second sensing electrode is removed. As illustrated in FIG. 4B, the first portion 130a and the second portion 130b of the first sensing electrode and the first portion 140a and the second portion 140b of the second sensing electrode define a sensing cavity 150 of the sensor. For example, the first portion 130a of the first sensing electrode and the first portion 140a of the second sensing electrode define a vertical sensing cavity 150a of the sensor, while the second portion 130b of the first sensing electrode and the second portion 140b of the second sensing electrode further define a lateral portion 150b of the vertical sensing cavity 150a of the sensor. The second portion 130b of the first sensing electrode and the second portion 140b of the second sensing electrode are electrically coupled to the conducting lines 117$_1$ and 117$_2$. The first portion 130a and the second portion 130b of the first sensing electrode and the first portion 140a and the second portion 140b of the second sensing electrode define the sensing cavity 150 with a zero dead volume.

The process as described allows integration of electronic sensors such as nanogap sensors over an IC chip with minimal or reduced mask count and planarization process, i.e., fewer and more simple processing steps. For example, the process for forming the sensors may include only two masks and one CMP step in a non-limiting example. For example, a single mask may be used to define the first sensing electrode and the second sensing electrode of the sensor(s). The process reduces the number of masks involved for integrating the sensor(s) with an IC chip. Additionally, a single CMP step may be used prior to removing at least a portion of the sacrificial layer. Further, the process is highly compatible with CMOS processing or technology. For example, the sensors may be formed on the CMOS substrate using CMOS processing.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. A device comprising:
   a substrate having conducting lines thereon;
   one or more fin structures arranged over the substrate;
   wherein each fin structure of the one or more fin structures comprises:
     a sensor arranged over the substrate and around each fin structure, wherein the sensor comprises a first sensing electrode and a second sensing electrode arranged around each fin structure, wherein the first sensing electrode and the second sensing electrode define a first sensing cavity along a first sidewall of each fin structure and a second sensing cavity along a second sidewall of each fin structure; and
     wherein the first sensing electrode and the second sensing electrode each comprises a first portion and a second portion arranged substantially perpendicular to the first portion, wherein the first portion of the first sensing electrode lines the first sidewall and the second sidewall of each fin structure and the first portion of the second sensing electrode lines the first sidewall and the second sidewall of each fin structure, wherein at least the first portion of the first sensing electrode and the first portion of the second sensing electrode define the first sensing cavity along the first sidewall and the second sensing cavity along the second sidewall, and wherein the second portion of the first sensing electrode and the second portion of the second sensing electrode are electrically coupled to the conducting lines.

2. The device of claim 1, wherein the first portion of the first sensing electrode completely overlaps the first portion of the second sensing electrode.

3. The device of claim 1, wherein the second portion of the first sensing electrode and the second portion of the second sensing electrode along the first sidewall and the second sidewall of each fin structure, respectively, are separated by sacrificial material.

4. The device of claim 1, wherein the first portion and the second portion of the first sensing electrode completely overlaps the first portion and the second portion of the second sensing electrode, respectively.

5. The device of claim 4, wherein the first sensing cavity and the second sensing cavity are vertical cavities with respect to a surface of the substrate.

6. The device of claim 1, wherein the first sensing electrode is electrically coupled to a first conducting line, and the second sensing electrode is electrically coupled to a second conducting line.

7. The device of claim 6, wherein the second sensing electrode comprises an extension region to contact the second conducting line.

8. The device of claim 7, wherein the extension region of the second sensing electrode is spaced apart from the first sensing electrode by a dielectric spacer.

9. The device of claim 1, wherein the one or more fin structures are each formed of a dielectric material.

10. The device of claim 1, wherein each of the first sensing cavity and the second sensing cavity is a nanogap channel.

11. The device of claim 1, wherein the one or more fin structures further comprises an array of fin structures arranged over the substrate.

12. The device of claim 1, wherein, for each fin structure of the one or more fin structures, the first sensing electrode and the second sensing electrode completely surrounds each fin structure.

13. The device of claim 1, wherein, for each fin structure of the one or more fin structures, the first sensing electrode and the second sensing electrode partially surrounds each fin structure.

14. The device of claim 1, wherein each of the first sensing cavity and the second sensing cavity is a vertical sensing cavity around each fin structure.

15. A method of forming a device, comprising:
   providing a substrate having conducting lines thereon;
   arranging one or more fin structures over the substrate;
   arranging a sensor over the substrate and around each fin structure of the one or more fin structures, wherein arranging the sensor comprises forming a self-aligned first sensing electrode and a self-aligned second sensing electrode around each fin structure of the one or more fin structures, wherein for each fin structure of the one or more fin structures,
     the first sensing electrode and the second sensing electrode define a first sensing cavity along a first sidewall of each fin structure and a second sensing cavity along a second sidewall of each fin structure; and wherein the first sensing electrode and the second sensing electrode each comprises a first portion and a second portion arranged substantially perpendicular to the first portion, wherein the first portion of the first sensing electrode lines the first sidewall and the second sidewall of each fin structure and the first portion of the second sensing electrode lines the first sidewall and the second sidewall of each fin structure, wherein at least the first portion of the first sensing electrode and the first portion of the second sensing electrode define the first sensing cavity along the first sidewall and the second sensing cavity along the second sidewall, and the second portion of the first sensing electrode and the second portion of the second sensing electrode are electrically coupled to the conducting lines.

16. The method of claim 15, wherein arranging the one or more fin structures over the substrate comprises depositing a dielectric layer over the substrate and patterning the dielectric layer to form the one or more fin structures.

17. The method of claim 15, wherein forming the self-aligned first sensing electrode and the self-aligned second sensing electrode around the one or more fin structures comprises:

depositing a first electrode layer over the one or more fin structures;
depositing a sacrificial layer over the first electrode layer;
depositing a second electrode layer over the sacrificial layer; and
removing at least a portion of first electrode layer, the sacrificial layer and the second electrode layer using a single mask to define the first sensing electrode and the second sensing electrode.

18. The method of claim 17, further comprising:
electrically coupling the second sensing electrode to one of the conducting lines by forming a dielectric spacer around the defined first sensing electrode and second sensing electrode; and
forming an extension region of the second sensing electrode over the dielectric spacer to contact the one of the conducting lines.

19. The method of claim 15, wherein the first portion of the first sensing electrode completely overlaps the first portion of the second sensing electrode.

20. The method of claim 15, wherein the first portion and the second portion of the first sensing electrode completely overlaps the first portion and the second portion of the second sensing electrode, respectively.

* * * * *